United States Patent [19]

Smis et al.

[11] Patent Number: 5,389,258
[45] Date of Patent: Feb. 14, 1995

[54] METHOD FOR THE ANAEROBIC DECOMPOSITION OF ORGANIC WASTE

[75] Inventors: Jan R. G. Smis, Melsen-Merelbeke; Luc. A. De Baere, De Pinte, both of Belgium

[73] Assignee: Organic Waste Systems, N.V., Belgium

[21] Appl. No.: 83,258

[22] Filed: Jun. 29, 1993

[30] Foreign Application Priority Data

Jun. 30, 1992 [BE] Belgium ............................. 09200605

[51] Int. Cl.⁶ ........................ C02F 11/04; C02F 3/28
[52] U.S. Cl. .................................. 210/603; 210/610; 210/630; 210/903
[58] Field of Search ............. 210/603, 903, 605, 608, 210/609–611, 614, 623, 630, 631, 906

[56] References Cited

U.S. PATENT DOCUMENTS

| | | | |
|---|---|---|---|
| 4,491,522 | 1/1985 | Ishida et al. | 210/603 |
| 4,684,468 | 8/1987 | De Baere | 210/603 |
| 4,735,724 | 4/1988 | Chynoweth et al. | 210/603 |
| 4,948,509 | 8/1990 | Stack | 210/603 |

Primary Examiner—Thomas Wyse
Attorney, Agent, or Firm—Bacon & Thomas

[57] ABSTRACT

Method for the anaerobic decomposition of degradable organic waste and for the extraction of biogas from the latter in a reactor (1), according to which method the waste is put in a reactor (1) which contains an active, anaerobic, methanogene biomass and which is exposed to anaerobic fermentation without any mixing in the reactor (1), characterized in that the waste is supplied in the shape of a semi-solid or solid organic substrate at the top of the reactor, in that a phase separation into a liquid phase (6) and a solid phase (4) is allowed in the lower part of the reactor, whereby at least during a fermentation period without any mixing in the reactor (1), a liquid phase (6) is secreted at the bottom in the reactor (1) from a top solid phase (4), in that this liquid phase (6) is removed before fresh substrate is supplied, whereby a maximum amount of solid phase (4), namely substrate and biomass, is retained, and in that, after the removal of the liquid phase (6), the solid phase (4) is removed from the reactor (1) to at least one third of the entire content of the reactor (1) and thoroughly mixed with fresh substrate as inoculum.

17 Claims, 2 Drawing Sheets

METHOD FOR THE ANAEROBIC DECOMPOSITION OF ORGANIC WASTE

BACKGROUND OF THE INVENTION

1. Field of the Invention

The present invention concerns a method for the anaerobic decomposition of degradable organic waste and for the extraction of biogas from the latter in a reactor, according to which method the waste is put in a reactor which contains an active, anaerobic, methanogene biomass and which is exposed to anaerobic fermentation without any mixing in the reactor.

By degradable organic waste is meant in particular the organic fraction of domestic or biological waste or similar organic fractions such as sludge, industrial organic waste, etc.

2. Description of Related Art

According to the known methods for the decomposition of domestic solid waste, or similar solid waste, water is added to the organic fraction of the solid waste, such that pulp is obtained containing 10 to 12% solid matter which is decomposed in an anaerobic manner. The waste is regularly supplied to a reactor for anaerobic decomposition in which the concentration of solid matter amounts to 4 to 8% and in which the waste is decomposed for 10 to 30 days at a temperature of about 35 to 50 degrees Celsius. The content of the reactor is regularly mixed, such that the freshly supplied waste makes contact with the already decomposed residue in the reactor.

With such methods, thorough mixing is important, such that the supplied waste is evenly distributed in the reactor and the methane bacteria make contact with their nutrients. Thus, the formation of inactive zones in the reactor can be avoided.

The concentration of dry matter, however, is limited in these entirely mixed, anaerobic reactors to about 8% at the most. This is mainly due to crustation, as a result of which the mixing is ineffective, and consequently inactive zones are formed or the reactor acidifies. Consequently, the gas production is limited to 1 to 1.5 $m^3$ biogas per $m^3$ waste per day.

Mixing and crustation problems in the treatment of the organic part of domestic waste, similar solid waste or semi-solid substrates and the ensuing low load level of the reactor and restricted gas production can be avoided by making use of dry or liquid two-phase, highly-efficient decomposition devices.

Dry anaerobic, highly efficient decomposition devices work with a solid concentration whereby no crustation or phase-separation takes place, and whereby the mixing is done by removing the content of the reactor from this reactor and by mixing it in an appropriate mixing device with supplied nutrient substrate and by subsequently pumping the mixture back in the reactor. By using high concentrations of solid matter, phase separation, and consequently crustation, is avoided and the production of biogas with a high output of 6 to 8 $m^3$ biogas per $m^3$ waste per day is possible. In fact, one could say that these devices work with the crust itself.

The dry anaerobic composting method, as described in EP-A-O 131 319 and EP-A-O 205 721 B1, whereby the organic fraction of the domestic waste is decomposed with a concentration of totally solid matter of 25 to 45%, is for example based on a thorough re-circulation of two thirds of the matter which was taken out of the reactor. This recycled material is then mixed as inoculum with an amount of fresh organic material equal to less than half of this recycled amount. However, this method is especially suited for dry, solid substrates, such that a high concentration of solid matter can be maintained in the reactor.

Liquid, two-phase, highly efficient decomposition devices, as opposed to the above-mentioned dry decomposition devices, work with a very low concentration of totally solid matter in the methanogene phase, and make use of a sludge bed reactor or other types of anaerobic reactors with a high water level for the treatment of waste waters with a low concentration of suspended solid matter.

In these devices, the organic fraction of the domestic or organic waste is preliminary treated in a shredder and hydrolysis tank, such that the biologically degradable fraction is made as liquid as possible. This preliminary treated fraction is separated by means of a press or other dehydrating means from the remaining solid matter, and the liquid containing less than 2 to 3% totally solid matter and whose solid matter is preferably dissolvable for more than 80%, is subsequently decomposed in an anaerobic upward sludge bed or similar reactor. This method is more suited for the easily hydrolysable and biologically degradable fraction of domestic waste, which is also the most humid fraction of the domestic waste.

SUMMARY OF THE INVENTION

The invention concerns a new method for anaerobic decomposition which is applicable to organic waste such as the organic fraction of domestic or biological waste or similar organic fractions such as sludge, industrial organic waste, etc., and which is also suited for the decomposition of other waste than dry solid substrates or the fraction of domestic waste which can be easily hydrolysed, but which nevertheless can be highly efficient.

To this aim the waste is supplied in the shape of a semi-solid or solid organic substrate at the top of the reactor, a phase separation into a liquid and solid phase is allowed in the lower part of the reactor, whereby at least during a fermentation period without any mixing in the reactor, a liquid phase is secreted at the bottom in the reactor from an upper solid phase, this liquid phase is removed before fresh substrate is supplied, whereby a maximum amount of solid phase, namely substrate and biomass, is retained, and, after the removal of the liquid phase, the solid phase is removed from the reactor to at least one third of the entire content of the reactor and thoroughly mixed with fresh substrate as inoculum.

The dry reactor can provide a high output without any internal mixing and a with a high concentration of solid matter, without it being required to maintain the concentration of solid matter at levels of 25 to 40% for extraction and fermentation purposes as is the case with the known dry anaerobic decomposition method. As opposed to this known dry anaerobic decomposition method, phase separation or crustation is allowed in this reactor. Said phase separation is used to remove all redundant liquids from the reactor, such that the reactor can work with a humid and biologically highly degradable substrate, but also with a high concentration of solid matter. If similar substrates were treated in a reactor with a high percentage of solid matter, material should be removed from the reactor and dehydrated to remove the surplus of water and to maintain the concentration of solid matter in the reactor at 25 to 40%.

The method according to the invention is also different from liquid, two-phase, highly-efficient devices in that the separation is carried out in one single tank and in that the phase separation is obtained by a natural phenomenon at the bottom of the reactor and not through sifting or dehydration. In these liquid, two-phase, highly efficient devices, the first phase is used for hydrolysis of the solid matter, after which the solid matter is removed and the liquid is exposed to an anaerobic sludge bed with a high output or any other type of liquid reactor with a high output. According to the invention, the hydrolysis and anaerobic degradation take place in the concentrated top part, and the phase separation or the removal of the redundant water, required to maintain a concentrated decomposition, takes place by removing liquid after a natural phase separation at the bottom in the reactor.

Preferably, the amount of fresh substrate is practically equal to the amount of liquid phase which has been removed from the reactor, increased by the amount which disappeared during the formation of said phase as biogas.

According to a special embodiment of the invention, the phase separation is allowed in the lower part of the reactor, preferably in the lower 0 to 20% of this reactor.

According to a peculiar embodiment of the invention, waste is supplied having such a percentage of dry matter that the percentage of dry matter of the content of the reactor, prior to the phase separation, is situated between 15 and 35%.

The organic waste to be decomposed can be supplied as such directly to the reactor. However, it is also possible that the waste supplied at the top of the reactor is composed by mixing solid or semi-solid waste with waste water.

According to this embodiment the waste water is treated simultaneously with the semi-solid or solid organic substrate, such that both the anaerobic disintegration of the solid or semi-solid nutrition and the anaerobic reduction of the pollution in the waste water flow takes place.

The invention also concerns a device which is particularly suited for the embodiment of the method according to any of the above embodiments.

Thus, the invention concerns a device for the anaerobic decomposition of organic waste contained in a closed reactor, a supply device connected to the top of the reactor for the supply of organic material to be decomposed, a discharge device connected to the bottom of the reactor for the discharge of the solid residue and a mixing device for mixing the discharged residue with fresh organic material, which is characterized in that the reactor contains a discharge device for discharging a liquid phase at the bottom of the reactor.

Preferably, the device contains filter means which are mounted at the bottom in the reactor so as to stop the solid phase as the liquid phase is discharged.

Practically, these filter means consist of partitions directed from the bottom to the top which are provided with passages, whereas the discharge device for the liquid phase contains discharge pipes to which said partitions lead.

In order to better explain the characteristics according to the invention, some preferred embodiments of a method and device for the anaerobic decomposition of organic waste are described below by way of example only and without being limitative in any way, with reference to the accompanying drawings.

DETAILED DESCRIPTION OF THE INVENTION

Figure 1:
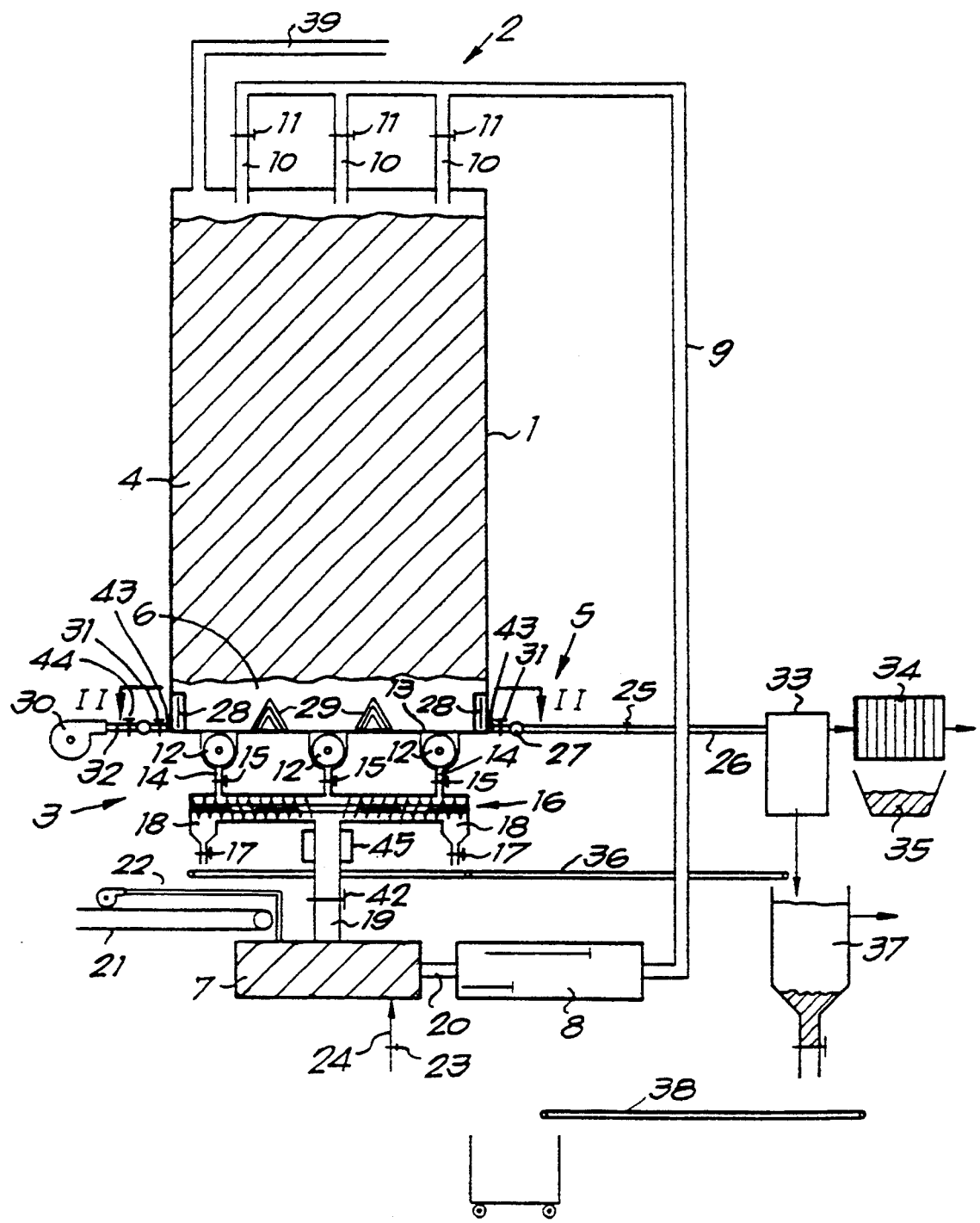
FIG. 1 is a schematic representation of a device for the anaerobic decomposition of organic waste according to the invention.
Figure 2:
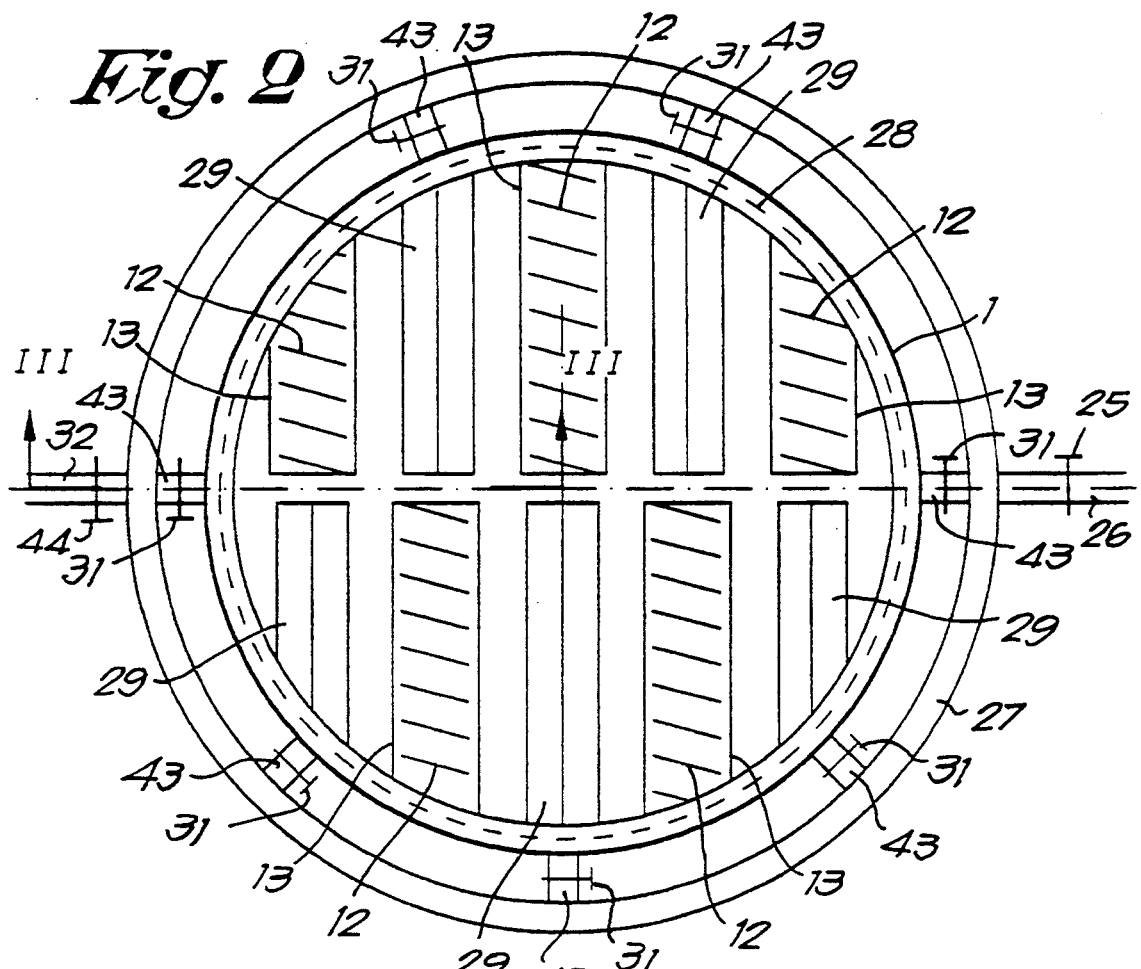
FIG. 2 shows a section according to line II—II in FIG. 1.

The device represented in FIG. 1 mainly contains a closed reactor 1, a supply device 2 for the nutrition of the reactor 1, a discharge device 3 for the solid residue, being the solid fermented phase 4, a discharge device 5 for the liquid residue of the liquid phase 6 and a mixing device 7, which is mounted between the supply device 2 and the discharge device 3, for the mixing of the fermented solid waste 4 with fresh organic material to be decomposed.

The supply device 2 consists of a displacement pump 8 and a supply pipe 9 which, via ramifications 10 provided with automatic valves 11, runs into the upper side of the reactor 1 at different places.

The discharge device 3 for the solid phase 4 contains a number of screw jacks 12 which are erected opposite grooves 13 in the bottom of the reactor 1 and which, via ducts 14 provided with valves 15, lead to a central discharge screw jack 16. Depending on the sense of rotation, said pump pumps towards both ends, where outlets 18 shut by valves 17 are normally connected, or to the center, where a central discharge pipe 19 is connected, which connects the jack 16 with the mixing device 7 and which can be shut by means of a valve 42.

The mixing device 7 is connected to the displacement pump 8 with its discharge pipe 20, whereas an endless conveyor belt 21 for fresh organic material leads to said mixing device 7, and a supply pipe 22 for the possible supply of waste water to the mixing device 7 and a steam piping 24 which can be shut by means of a valve 23 run into said device 7.

The discharge device 5 for the liquid phase 6 contains a discharge pipe 26 which can be shut by means of a valve 25, which is connected to a closed ring line 27 which surrounds the bottom of the reactor 1 and which leads to the bottom of the reactor 1 via filters 28 and 29. The filters 28 are built in upright in the wall of the reactor, whereas the filters 29 are sheets provided with openings which stand two by two at the bottom of the reactor sloping as a hood and which form a space which reaches to the reactor wall with both ends. Said two ends and the filters 29 lead via pipes 43 which can be shut by means of valves 31 to the ring line 27, as represented in detail in FIG. 3. In order to freely rinse the filters when they are obstructed, a rinsing pipe 32 connected to a pump 30 and which can be shut by means of a valve 44 is connected to the ring line 27. The discharge pipe 26 is connected to a press filter 34 or another water treatment device via a storage tank 33. Remaining solid parts are collected in a reservoir 35. The storage tank 33 can be provided for the application of an anaerobic fermentation or nitrification for a certain time.

Under the outlets 18, a conveyor belt 36 is erected which leads to a settling tank 37, from where the sediment can be discharged to a water treatment device via a conveyor belt 38 and the liquid phase.

At the top, a discharge pipe 39 for biogas is connected to the reactor 1.

The device operates and is used as follows:

When the device is started up, the reactor 1 is filled via the supply device 2 with anaerobic inoculum. Said inoculum may be provided by a well working anaerobic reactor with a high percentage of solid matter such as a reactor described in patent EP-A-O 131 319, or it can be made by dehydrating the fermented residue of a well working, entirely mixed anaerobic reactor which preferably decomposes the organic fraction of household waste, sewer sludge, manure, biomass or any other organic substrate, or on the basis of the sludge of an upward flow sludge bed reactor which purifies waste water under anaerobic circumstances. The inoculum contains common anaerobic micro-organisms such as species of Methanosarcina, Methanothrix, Methanosoenghenii, etc. for anaerobic decomposition. The inoculum contains at least 15% and preferably 25 to 35% totally solid matter. The amount of inoculum to start with is preferably as large as possible, preferably sufficient to fill the entire content of the reactor 1. The inoculum is heated up to mesophile temperatures (35 to 40 degrees Celsius) or thermophile temperatures (50 to 55 degrees Celsius). Then the inoculum is removed again from the reactor by means of the discharge device 3, thoroughly mixed in the mixing device 7 with preferably not more than 10 to 20 weight % of the organic material to be decomposed whose size has preferably been reduced during a preliminary treatment, which has been supplied via the conveyor belt 21 and has been brought back in the reactor 1 by the pump 8 via the pipe 9 and the ramifications 10, where the substrate is left alone.

Due to the highly active bacteria in the inoculum, the static decomposition immediately takes place in the reactor 1 without any mixing and the natural phenomenon of phase separation into a solid phase 4 at the top and a liquid phase 6 in the lower part, preferably the lower 0 to 20% of the reactor 1, is started. This phenomenon is not hindered in any way, but on the contrary allowed. After one or several hours, depending on the nature of the substrate and the percentage of dry matter in the solid phase 4, the secretion of liquid phase 6 has advanced sufficiently, such that said phase can be discharged.

Said extraction of liquid phase is started by opening the valves 25. The extraction takes place in various places at the bottom of the reactor 1 through the filters 28 and 29 which stop as much solid matter as possible in the liquid phase, such that a liquid with a minimum amount of suspended solid matter is discharged. This liquid is carried to the storage tank 33 which may be provided to allow for an anaerobic fermentation to further purify the liquid or to allow for a nitrification, possibly a denitrification, therein to reduce the amount of ammonium nitrogen and the amount of nitrates respectively. The low-nitrogen liquid can then be carried back to the reactor 1 via the pipe 22.

After the extraction of the liquid phase, an amount of fresh organic material, whose weight is about equal to the amount of liquid which was removed, increased by the amount of material which has been removed via the biogas, is supplied to the mixing device 7 via the conveyor belt 21 and subsequently mixed with a part, namely ⅓ of the total amount of material, i.e. the solid phase which remains in the reactor 1 with regard to the total amount of said material, for example with half of the solid phase in the reactor or with the entire solid phase in the reactor. The weight proportion of the material from the reactor 1, which is in fact the inoculum, to the amount of fresh organic material may be higher than 3:1 and may be situated for example between 8:1 and 10:1. This part of the solid phase is supplied in the mixing device 7 by means of the screw lacks 12 and the central screw jacks 16 via the central discharge pipe 19.

The percentage of dry matter of the mixture is situated between 15 and 40% and preferably between 15 and 35%. Within these limits, an amount of waste water or ordinary water may be supplied to the mixing device 7 via the supply pipe 22 if required. Preferably, water or waste water with a low percentage of nitrogen and salts is added, such that during the subsequent phase separation the possible excess of nitrogen and salts from the fresh organic material ends up in the liquid phase, which promotes the disintegration.

In case of a high amount of nitrogen in the solid phase the liquid phase can be partly nitrified, possibly denitrified in the storage tank 33 and supplied again to the reactor 1 via the pipe 22 and the pump 8. In this way, excess nitrogen from the solid phase 4 is extracted. After the nitrification/denitrification the liquid phase may also be centrifuged or pressed, after which only the low-nitrogen cake from the centrifuge or, when a press is used, the pressed cake is recycled towards the reactor 1. By adding steam via the steam pipe 24, the mixture in the mixing device 7 is heated up to 35–40 or 50–55 degrees Celsius.

The mixture is pumped into the reactor 1 from the mixing device 7 via the pipe 9 and the ramifications 10 through the pump 8. The discharge device 5 is closed and the valve 25 is shut. Also the discharge device 3 is inoperative and the screw jacks 12 are out of action. The content of the reactor 1 is left be, for example for one night, whereby a separation into a liquid phase 6 in the lower part, preferably the lower 0 to 20%, and a solid phase 4 on top of it again takes place. Afterwards, said liquid phase 6 is discharged from the reactor 1 in the manner described above, and subsequently at least one third of the content of the reactor 1 of solid phase 4 is put from the reactor 1, also as described above, into the mixing device 7 and mixed there with about the same amount of fresh organic material as the amount of discharged liquid phase and biogas.

The above-mentioned stages are then successively repeated, whereby from time to time, for example once a week, right after an extraction of the solid phase 4, a rinsing of the screw jacks 12 and 16 is carried out, such that there is no solid phase anymore so that, during the following phase separation, these pumps will be filled with liquid phase 6. Hereby, also heavy particles such as glass, metal, etc. which are present in the reactor 1, will settle and end up at the bottom of the reactor and in said screw jacks 12 and 16. By subsequently driving the central screw jack 16 such that it pumps towards the outlets 18, these heavy particles can be discharged via said outlets 18, whose valve 17 was temporarily opened. These particles are collected on the conveyor belt 36 and transported to the settling tank 37 to which, if required, liquid from the storage tank 33 can be added so as to obtain a good sedimentation and separation.

The sediment of the tank 37 is discharged via the conveyor belt 38. The discharged liquid phase 6, which still contains a percentage of dry matter of 2 to 5%, is carried via the discharge pipe 26 to the storage tank 33 and from there via the press filter 34 or via other suitable equipment to a water treatment device. The pressed cake is collected in the reservoir 35 and possibly further re-composted in an aerobic manner.

Figure 3:
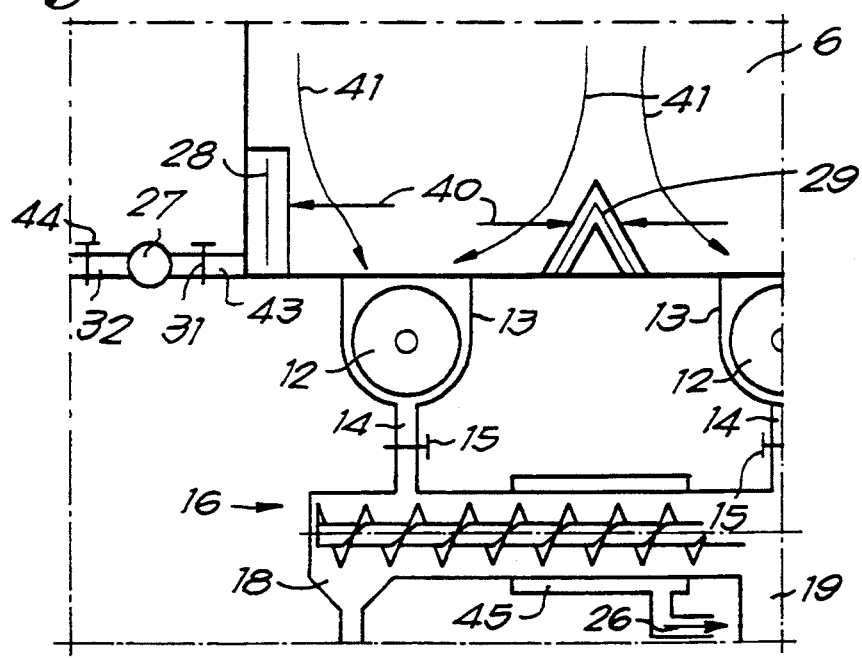
FIG. 3 shows a section according to line III—III in FIG. 2, to a larger scale.

The filters 28 and 29 in the wall and at the bottom of the reactor are self-cleaning because the liquid flow, as indicated by the arrow 40 in FIG. 3, is horizontal during the extraction, whereas during the removal of the solid phase 4 from the reactor, the flow runs vertically, as indicated in FIG. 3 by the arrows 41. This implies that the particles of a layer of solid matter which are retained by the vertically or slantingly erected filters 28 and 29 are removed during the liquid extraction by the downward movement of the solid phase during the extraction of said solid phase.

On the central screw jack 16 may be mounted a double-walled cage with filter means 45, as indicated in FIG. 1, such that also the liquid phase 6 can be extracted via this cage 45. The central screw jack 16 can be built such that a pressure is created in it such that extra liquid is pressed through the cage with filter means 45 during the extraction of the solid phase 4. Also, during the phase separation, secretion of the liquid phase 6 may take place via this cage if the screw jack 16 is sufficiently discharged of solid phase 4 and contains mainly liquid phase 6.

Extra filter means such as cages 45 can be mounted around the screw jacks 12 for the extraction of the liquid phase 6. Such cages are only represented in FIG. 3.

Also the filter means 45 are self-cleaning thanks to the two different directions of the liquid phase 6 and the solid phase 4 respectively. If such filter means 45 are provided, it is possible to leave the extraction filters 29 out, in which case the bottom of the reactor 1 is flat and a slide frame as described in EP-A-0 205 721 can be mounted such that it can slide to and fro so as to push the solid phase 4 in the grooves 13.

Should the filters 28 and 29 become obstructed, they can be cleaned by pumping liquid counterflow through the filters by means of the pump 30 via the rinsing pipe 32 with temporarily opened valve 31, whereby by shutting the pipes 43 with which they are connected via the ring line 27, the filters to be cleaned can be isolated from the others.

If, due to very strong decomposition or due to loss via the liquid phase 6, the amount of solid phase 4 decreases too strongly, this may be replenished by adding peat, straw, newsprint or any other organic material in which bacteria can be retained, such that there is always sufficient biomass in the reactor.

If, due to strong decomposition or a high percentage of nitrogen in the fresh substrate, the percentage of nitrogen in the solid phase 4 becomes too high, peat, paper, organic waste or pressed cake, collected in the reservoir 35 and aerobically re-composted through nitrification and denitrification, may be added in the reactor 1 so as to reduce the nitrogen percentage in the solid phase 4 and also increase the percentage of dry matter. The percentage of nitrogen is reduced to less than 2 to 4 grams ammonium nitrogen per kilogram of solid phase 4, whereas the amount of nutrients in the solid phase is kept optimum, such that a fast anaerobic decomposition is obtained.

The above-described method allows for maximum retention times of biomass in the reactor by keeping the biomass in the solid phase, and makes it possible to work with a high concentration of solid matter of 15 to 30%, making use of the natural separation between liquid and solid phase in a semi-solid reactor. A high biogas production of 4 to 8 $m^3$ per $m^3$ reactor per day which is discharged via the discharge pipe 39 is obtained. If waste water is supplied to the nutrients of the reactor 1, this waste water is simultaneously decomposed and an extra amount of biogas is obtained, and an extra amount of liquid phase must be removed at every liquid extraction from the reactor. This makes it possible to simultaneously treat waste water and organic waste.

The speed of the phase separation will depend from the percentage of dry matter in the content of the reactor 1. With a percentage of dry matter of 18% instead of for example 22%, the phase separation will take place faster. Said percentage of dry matter can be changed by adding waste water of dry organic material such as peat, straw, etc. The speed can also be influenced by changing the matrix contained in the active biomass. Said matrix may consist of a support material such as sponges or peat, or also of recycled re-composed pressed cake.

The method will become clear from the following examples:

EXAMPLE 1

400 tons/week of an organic waste flow with a percentage of solid matter of 23%, for example originating from a selective household refuse collection, of which 92% of the solid matter can be evaporated and can be easily degraded in a biological manner, was gradually put into the above-described reactor with a capacity of 2500 $m^3$ in the above-described manner. After each extraction of an amount of liquid phase and simultaneously an amount of biogas, about the same amount of this waste flow was mixed in the mixing device with solid phase which had been taken from the reactor according to a ratio 1:9. Only steam (30 tons/week) was added to this mixture so as to heat it up. The heated mixture was then supplied to the reactor by the supply device.

95% of the biologically degradable solid matter which could be evaporated was transformed into biogas in a period of 20 days with a biogas production of 90 tons/week. The total percentage of solid matter in the solid phase amounted to 18%. The amount of discharged liquid phase was 340 tons/week. This phase still contained a weight percentage of 3.7% solid particles.

EXAMPLE 2

The example 1 was repeated, but 400 tons/week of waste water with a percentage of solid matter of 2%, of which 90% can be evaporated and 90% thereof are biologically degradable, were added to the mixing device.

The biogas production amounted to 98 tons/week. The amount of discharged liquid phase was 732 tons/week with a percentage of solid matter of 2.1%.

The above-described method is very simple. The output and biogas production are higher than with an entirely mixed reactor, whereas organic waste with a percentage of dry matter which is too low for dry decomposition can nonetheless be treated. In some cases, an amount of waste water can be simultaneously treated, without having to enlarge the reactor.

Solid or semi-solid substrates with a high percentage of nitrogen can also be optimally treated in the reactor since, due to the phase separation, the excess of ammonium nitrogen ends up in the liquid phase and is discharged. In order to facilitate the discharge of ammonium nitrogen, liquid such as water or waste water with a low percentage of nitrogen can be added to the substrate. Should the nitrogen percentage be too high in the solid phase, peat as well as organic material containing little nitrogen, such as aerobically re-composted pressed cakes or centrifuged sludge after nitrification of the liquid phase in particular, can be added to the solid phase.

Substrates with a high percentage of salts can be treated in a similar manner as, due to the phase separation most salts end up in the liquid phase and are discharged. In order to further promote the removal of salts, liquid such as water or waste water with a low salt content can be added to the substrate. Should the salt content be high, the liquid phase, after desalination by means of the appropriate equipment, can be supplied to the reactor. The adding of water, waste water with a low salt content or recycled liquid phase to the solid phase is done to such extent that the electrical conductivity of the solid phase, when diluted with water to 1:5, is less than 1.5 milliSiemens per centimeter.

The invention is in no way limited to the above-described embodiments; on the contrary, many modifications can be made to the described embodiments within the scope of the claims, among others as far as the form of the reactor and the working conditions are concerned.

In particular, the filters at the bottom of the reactor must not necessarily have the described form. The filters or one of the filters may for example consist of a conical perforated wall which is erected in the lower end of the reactor. The space between said wall and the wall of the reactor can then form the ring line. However, each of the filters can also be directly connected to a separate lockable discharge. Instead of containing a flow back device for the cleaning of the filters or as an extra accessory, scrapers or other mechanisms can be mounted on these filters so as to remove solid particles from the filters.

We claim:

1. A method for the anaerobic decomposition of degradable organic waste and for the extraction of biogas from the latter in a reactor containing an active, anaerobic, methanogene biomass which is exposed to anaerobic fermentation without any mixing in the reactor, comprising
   supplying waste in the form of a semi-solid or solid organic substrate at the top of said reactor,
   allowing phase separation into a liquid phase and a solid phase in the lower part of said reactor,
   secreting a liquid phase at the bottom of said reactor from a top solid phase during a fermentation period without any mixing in said reactor,
   removing said secreted liquid phase before fresh waste is supplied to said reactor,
   removing at least one third of the entire content of the solid phase from said reactor and thoroughly mixing it with fresh substrate to form said waste which is supplied at the top of said reactor.

2. The method according to claim 1, wherein the amount of fresh waste mixed with the solid phase is about equal to the amount of liquid phase which is removed from the reactor as liquid and biogas.

3. The method according to claim 1, wherein the phase separation occurs in the lower part of said reactor.

4. The method according to claim 3, wherein the phase separation occurs in the lower 0 to 20% of said reactor.

5. The method according to claim 1, wherein the dry matter content of said reactor after supplying the waste and before phase separation is between 15 and 25%.

6. The method according to claim 1, further comprising mixing said waste with waste water before supplying it at the top of said reactor.

7. The method according to claim 1, further comprising mixing peat, paper, organic waste or aerobically re-composted pressed cake with said waste before it is supplied at the top of said reactor such that the nitrogen percentage in the solid phase in the reactor is maintained lower than 2 to 4 grams of ammonium nitrogen per kilogram of solid phase and sufficient nutrients are provided for a fast anaerobic decomposition.

8. The method according to claim 1, further comprising mixing water or low-nitrogen waste water or nitrified liquid phase with said waste before it is supplied at the top of said reactor such that any excess of nitrogen is removed from the solid phase in the reactor.

9. The method according to claim 1, further comprising mixing an extra amount of water or waste water with a low salt content or recycled liquid phase from which the salts have been removed, with said waste, such that the solid phase has a low salt content and the specific electrical conductivity, when diluted with water to 1:5, is less than 1.5 milliSiemens per centimeter.

10. The method according to claim 1, further comprising periodically during phase separation, before removing the liquid phase, separating and discharging solid particles from the reactor.

11. The method according to claim 1, wherein the ratio of the solid phase removed from said reactor to fresh substrate in said waste is greater than 3:1.

12. The method according to claim 1, wherein said ratio is between 8:1 and 10:1.

13. The method according to claim 1, wherein the part of the solid phase which is removed from the reactor and mixed with fresh substrate, amounts to about half of the solid phase which remained in the reactor after the removal of the liquid phase.

14. The method according to claim 1, wherein the part of the solid phase which is removed from the reactor and mixed with fresh substrate is the entire solid phase which remained in the reactor after the removal of the liquid phase.

15. The method according to claim 1, further comprising purifying the liquid phase which is removed from the reactor by means of a press filter and re-composting the pressed cake from said press filter in an aerobic manner and mixing said re-composed pressed cake with the fresh substrate and solid phase which has been removed from the reactor.

16. The method according to claim 1, further comprising exposing the liquid removed from the reactor to a nitrification/denitrification and/or desalination treatment and mixing at least a part of the liquid so treated with the fresh substrate and solid phase which has been removed from the reactor.

17. The method according to claim 1, further comprising exposing the liquid removed from the reactor to an anaerobic wet fermentation and mixing at least a part of the fermented liquid with the fresh substrate and solid phase which has been removed from the reactor.

* * * * *